(12) United States Patent
Kim et al.

(10) Patent No.: US 9,903,705 B2
(45) Date of Patent: Feb. 27, 2018

(54) APPARATUS FOR FOCUS CONTROL AND METHOD FOR MANUFACTURING SEMICONDUCTOR DEVICE

(71) Applicant: Samsung Electronics Co., Ltd., Suwon-si, Gyeonggi-do (KR)

(72) Inventors: Kwang-soo Kim, Pyeongtaek-si (KR); Harutaka Sekiya, Yokohama (JP); Kwang-jun Yoon, Suwon-si (KR); Sung-won Park, Yongin-si (KR); Young-duk Kim, Seongnam-si (KR); Heon-ju Shin, Yongin-si (KR); Byeong-hwan Jeon, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/206,613

(22) Filed: Jul. 11, 2016

(65) Prior Publication Data

US 2017/0108329 A1   Apr. 20, 2017

(30) Foreign Application Priority Data

Oct. 14, 2015  (KR) ........................ 10-2015-0143372

(51) Int. Cl.
*G01N 21/00* (2006.01)
*G01B 11/00* (2006.01)
(Continued)

(52) U.S. Cl.
CPC ....... *G01B 11/002* (2013.01); *G01N 21/9501* (2013.01); *G01N 21/956* (2013.01); *H01L 21/681* (2013.01); *G01N 2201/121* (2013.01)

(58) Field of Classification Search
CPC ... G01N 2021/8867; G01N 2021/8887; G01N 21/211; G01N 21/31; G01N 21/55;
(Continued)

(56) References Cited

U.S. PATENT DOCUMENTS 7,488,924 B2    2/2009  Bublitz et al.
2007/0201019 A1  8/2007  Yamashita et al.
(Continued)

FOREIGN PATENT DOCUMENTS

KR   2001-0048755 A    6/2001
KR   10-2006-0004963 A   1/2006
(Continued)

*Primary Examiner* — Michael P Stafira
(74) *Attorney, Agent, or Firm* — Harness, Dickey & Pierce, P.L.C.

(57) ABSTRACT

An automatic focus control apparatus includes a light detector, which receives light reflected by a surface of a wafer and generates a light reception signal based on the received signal, a controller, which generates a driving signal, the driving signal being one of a first signal and a second signal, the driving signal indicating whether to perform automatic focus control based on the light reception signal, a focus error corrector, which generates a focus error correction signal based on the driving signal, and a stage driver, which displaces a wafer stage supporting the wafer by adjusting the z-axis position of the wafer stage based on the focus error correcting signal if the driving signal is the first signal, and maintains the z-axis position of the wafer stage based on the focus error correction signal if the driving signal is the second signal.

14 Claims, 15 Drawing Sheets

(51) Int. Cl.
    *H01L 21/68*     (2006.01)
    *G01N 21/95*     (2006.01)
    *G01N 21/956*     (2006.01)

(58) Field of Classification Search
    CPC ........... G01N 21/8851; G01N 2201/02; G01N 2201/06113; G01N 2201/101; G01B 11/0625; G01B 11/24; G01B 11/303; G02B 26/0808
    See application file for complete search history.

(56) References Cited

U.S. PATENT DOCUMENTS

| | | | |
|---|---|---|---|
| 2012/0287424 A1* | 11/2012 | Hori | G03F 1/84 |
| | | | 356/237.1 |
| 2012/0312957 A1* | 12/2012 | Loney | G02B 21/245 |
| | | | 250/201.3 |
| 2013/0293879 A1 | 11/2013 | Honda et al. | |
| 2014/0036245 A1 | 2/2014 | Sogard | |
| 2014/0152796 A1 | 6/2014 | Mitsuhiro et al. | |

FOREIGN PATENT DOCUMENTS

| | | |
|---|---|---|
| KR | 10-2011-0023992 A | 3/2011 |
| KR | 10-2014-0001366 A | 1/2014 |

* cited by examiner

APPARATUS FOR FOCUS CONTROL AND METHOD FOR MANUFACTURING SEMICONDUCTOR DEVICE

CROSS-REFERENCE TO RELATED APPLICATION

This application claims the benefit of Korean Patent Application No. 10-2015-0143372, filed on Oct. 14, 2015, in the Korean Intellectual Property Office (KIPO), the disclosure of which is incorporated herein in its entirety by reference.

BACKGROUND

1. Field

Inventive concepts relate to automatic focus controlling apparatuses for preventing and/or limiting a defocus, and methods of manufacturing semiconductor devices by using the automatic focus controlling apparatuses.

2. Description of Related Art

Along with miniaturization of electronic devices, patterns of semiconductor devices are becoming finer, and as such apparatuses for visual inspection of the semiconductor devices perform automatic focus control to obtain clearer images of the finer patterns.

SUMMARY

Inventive concepts provide an automatic focus controlling apparatus, and an automatic focus controlling apparatus method for preventing and/or limiting defocusing of the finer patterns formed on the semiconductor devices.

Inventive concepts also provide a method of manufacturing a semiconductor device by using the automatic focus controlling apparatus.

According to inventive concepts, there is provided a focus control apparatus including a light detector configured to receive reflected light reflected by a surface of a wafer and generate a light reception signal based on the received light; a controller configured to generate a driving signal including a first signal and a second signal, the driving signal indicating whether to perform focus control by using the light reception signal; a focus error corrector configured to generate a focus error correction signal based on the driving signal; and a stage driver configured to displace a wafer stage supporting the wafer by adjusting a z-axis position of the wafer stage based on the focus error correcting signal if driving signal is the first signal, and maintaining the z-axis position of the wafer stage if the driving signal is the second signal.

According to an example embodiment of inventive concepts, the first signal causes generation of the focus error correcting signal, thereby adjusting the z-axis position of the wafer stage, and the second signal prevents and/or limits generation of the focus error correcting signal, thereby holding the z-axis position of the wafer stage.

According to an example embodiment of inventive concepts, when the driving signal is switched from the second signal to the first signal, the z-axis position of the wafer stage is adjusted within about 2 micro-meters from a z-axis position of the wafer stage corresponding to the first signal is switched to the second signal.

According to an example embodiment of inventive concepts, the controller includes a light intensity measurer configured to measure a light intensity value of light incident to the light detector; and a driving signal generator configured to generate the first signal if the light intensity value is equal to or greater than a pre-set and/or selected reference value, and, generate the second signal if the total light intensity value is smaller than the reference value.

According to an example embodiment of inventive concepts, the light detector includes a split light receiving device having a light receiving surface split into four light receiving components, and the light intensity measurer calculates the total light intensity value by summing values respectively measured by the four light receiving components.

According to an example embodiment of inventive concepts, the controller includes an area signal generator configured to generate an area signal based on the location of the inspection point on the inspection surface, the area signal corresponding to an inspection area or a non-inspection area of the wafer; and a driving signal generator configured to generate the first signal if the area signal corresponds to the inspection area, and generate the second signal if the area signal corresponds to the non-inspection area.

According to an example embodiment of inventive concepts, the area signal generator includes a wafer map storage, which stores location coordinates of the inspection area and the non-inspection area; and a map combiner configured to generate the area signal corresponding to the location of the inspection point based on the location coordinates.

According to an example embodiment of inventive concepts, the focus control apparatus, further including an XY location corrector configured to receive the area signal and, generate an X-Y location correction signal if the area signal corresponds to the non-inspection area al, wherein the stage driver is further configured to adjust the x-axis position or the y-axis position of the wafer stage based on the X-Y location correcting signal.

According to an example embodiment of inventive concepts, the controller includes a light intensity measurer configured to measure a light intensity value of light incident to the light detector; an area signal generator configured to generate an area signal based on a location of an inspection point on the surface of the wafer, the area signal corresponding to the inspection area or the non-inspection area, and a driving signal generator configured to generate the first signal if the light intensity value is equal to or greater than a pre-set and/or selected reference value and the area signal corresponds to the inspection area, and generate the second signal if the light intensity value is smaller than or equal to the reference value and the area signal corresponds to the non-inspection area.

According to another example embodiment of inventive concepts, there is provided a method of manufacturing a semiconductor device, the method including preparing a wafer; and manufacturing a semiconductor device on the wafer, wherein the manufacturing of the semiconductor device includes scanning and inspecting an inspection surface of the wafer by using automatic focus control, and the inspecting of the inspection surface includes arranging the wafer on a wafer stage; irradiating light onto the surface of the wafer, receiving reflected light reflected by the surface of the wafer, and generating a light reception signal; generating a driving signal for determining whether to perform focus control by using the light reception signal; adjusting a z-axis position of the wafer stage if the driving signal is a first signal; and holding the z-axis position of the wafer stage if the driving signal is a second signal.

According to an example embodiment of inventive concepts, the method further includes, before the generating of the driving signal, measuring a light intensity value of reflected light reflected by the surface, wherein, in the generating of the driving signal, if the total light intensity value is equal to or greater than the reference value, the first signal is generated and, if the total light intensity value is smaller than the reference value, the second signal is generated.

According to an example embodiment of inventive concepts, the method further includes, determining inspection area on the surface prior to the generating of the driving signal; and generating an area signal corresponding to the inspection area or the non-inspection area based on the location of the inspection point on the surface, the generating of the area signal generates the area signal prior to generating of the driving signal, wherein, in the generating of the driving signal, if the area signal corresponds to the inspection area, the first signal is generated and, if the area signal corresponds to the non-inspection area, the second signal is generated.

According to an example embodiment of inventive concepts, the method further includes, before the generating of the area signal, an initial inspection point is set to be located within the inspection area, and the initial z-axis position of the wafer stage is adjusted, such that the initial inspection point is focused.

According to an example embodiment of inventive concepts, the method further includes, after the generating of the area signal, if the area signal corresponds to the non-inspection area, adjusting the x-axis position or the y-axis position of the wafer stage, such that the inspection point is located within the inspection area.

According to an example embodiment of inventive concepts, the inspection area is a cell area or a peripheral area.

According to an example embodiment of inventive concepts, a focus controlling apparatus may include a controller configured to, measure an intensity value of light reflected from a surface of a wafer, and determine whether to perform focus control on the wafer based on at least one of (i) the measured intensity value of the light reflected being equal to or greater than a reference value and (ii) an inspection point on the wafer being within an inspection area; and a stage driver configured to adjust a z-axis position of a wafer stage based on the determination, the wafer on the wafer stage.

According to an example embodiment, the controller may be further configured to output a driving signal based on the determination, the driving signal being one of a first signal or a second signal.

According to an example embodiment, the first signal may be generated by the controller if (i) the measured intensity value of the light reflected is equal to or greater than the reference value, and (ii) the inspection point on the wafer is in the inspection area, and the second signal is outputted by the controller if (i) the measured intensity value of the light reflected is less than the reference value, or (ii) the inspection point on the wafer is in the non-inspection area.

According to an example embodiment, the controller may include an area signal generator, the area signal generator may be configured to generate an area signal, the area signal corresponds to coordinates of the inspection point at which an inspection is performed based on a wafer map, and the area signal may indicate whether the inspection point on the wafer is within the inspection area.

According to an example embodiment, the focus controlling apparatus may further comprise a focus error corrector configured to generate a focus error correcting signal based on the driving signal, the focus error correcting signal adjusts the z-axis position of the wafer stage; and a location correction configured to generate a location correcting signal based on an area signal corresponding to a non-inspection area, the location correcting signal adjusts x and y axis positions of the wafer stage.

BRIEF DESCRIPTION OF THE DRAWINGS

Example embodiments of inventive concepts will be more clearly understood from the following detailed description taken in conjunction with the accompanying drawings in which.

DETAILED DESCRIPTION OF EXAMPLE EMBODIMENTS

Figure 1:
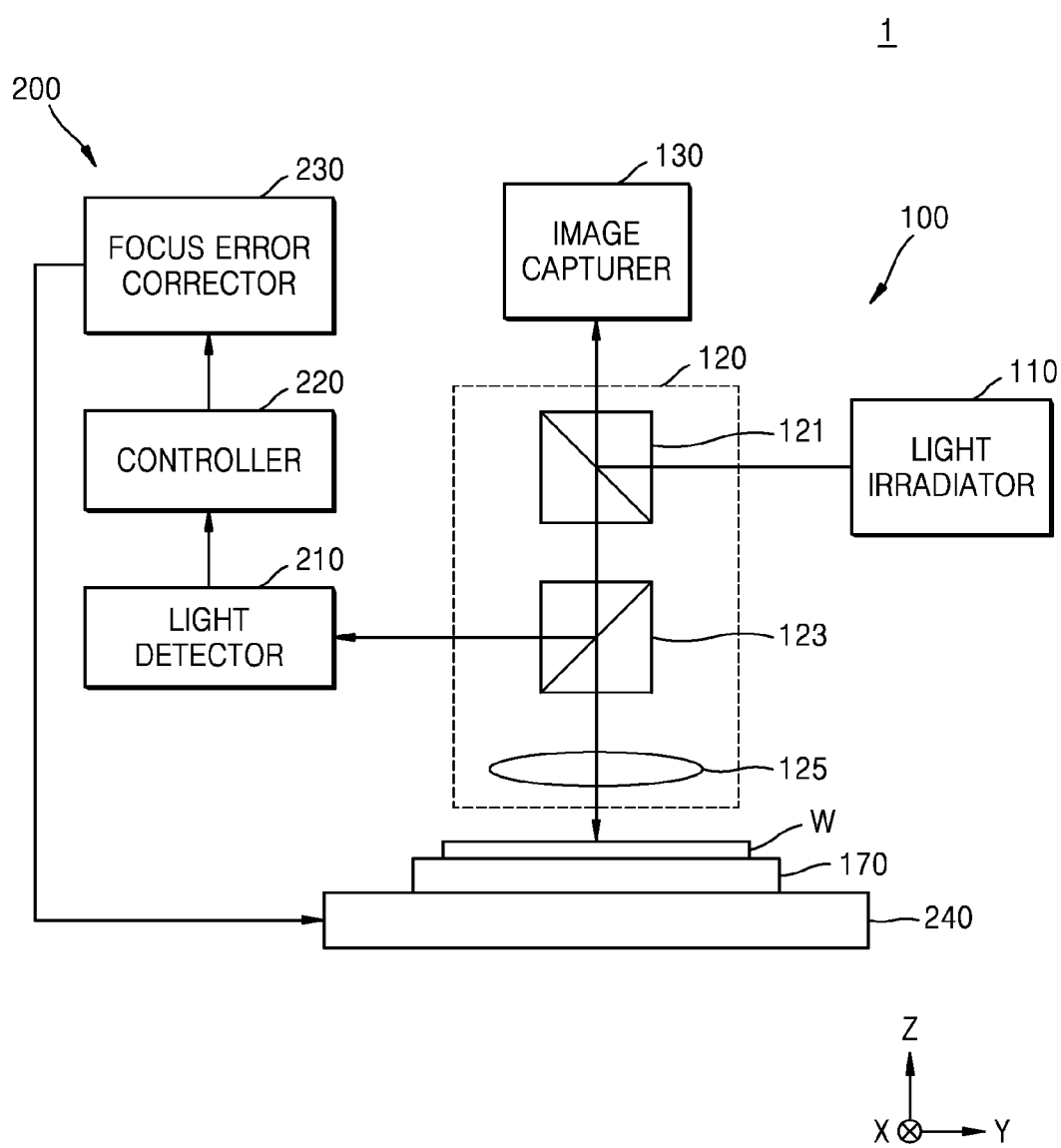
FIG. 1 is a diagram schematically showing a semiconductor inspection system according to an embodiment of inventive concepts.

As used herein, the term "and/or" includes any and all combinations of one or more of the associated listed items. Expressions such as "at least one of," when preceding a list of elements, modify the entire list of elements and do not modify the individual elements of the list.

Hereinafter, inventive concepts will be described more fully with reference to the accompanying drawings, in which example embodiments of inventive concepts are shown. Inventive concepts may, however, be embodied in many different forms and should not be construed as limited to the example embodiments set forth herein. Rather, these example embodiments are provided so that this disclosure will be thorough and complete, and will fully convey the scope of inventive concepts to those skilled in the art. In the drawings, lengths and sizes of layers and regions may be exaggerated for clarity.

It will be understood that when an element or layer is referred to as being "connected" or "coupled" another element or layer, the element or layer can be directly connected or coupled to another element or layer or intervening elements or layers. In contrast, when an element is referred to as being "directly on" another element or layer, there are no intervening elements or layers present. Like numbers refer to like elements throughout. As used herein, the term "and/or" includes any and all combinations of one or more of the associated listed items.

It will be understood that, although the terms "first," "second," "third," etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of inventive concepts.

Spatially relative terms, such as "upper," "above," "below," or "lower" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Example embodiments of inventive concepts are described herein with reference to cross-section illustrations that are schematic illustrations of example embodiments (and intermediate structures) of inventive concepts. As such, variations from the shapes of the illustrations as a result, for example, of manufacturing techniques and/or tolerances, are to be expected. Thus, example embodiments of inventive concepts should not be construed as limited to the particular shapes of regions illustrated herein but are to include deviations in shapes that result, for example, from manufacturing.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof. Expressions such as "at least one of," when preceding a list of elements, modify the entire list of elements and do not modify the individual elements of the list.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a diagram schematically showing a semiconductor inspection system 1 according to an example embodiment of inventive concepts.

Figure 2:
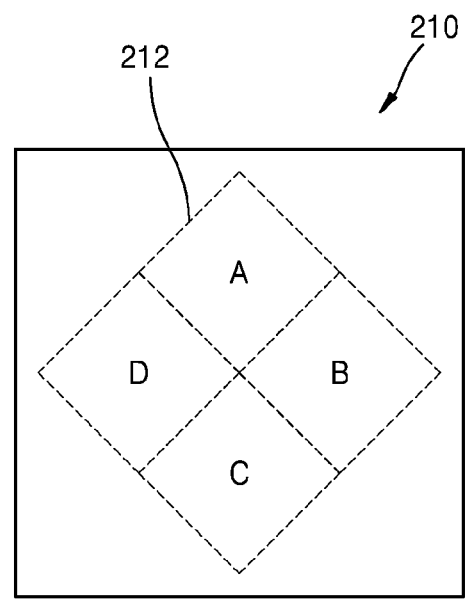
FIG. 2 is a diagram schematically showing a light detector according to an embodiment of inventive concepts.

FIG. 2 is a diagram schematically showing a light detector according to an example embodiment of inventive concepts.

Figure 3:
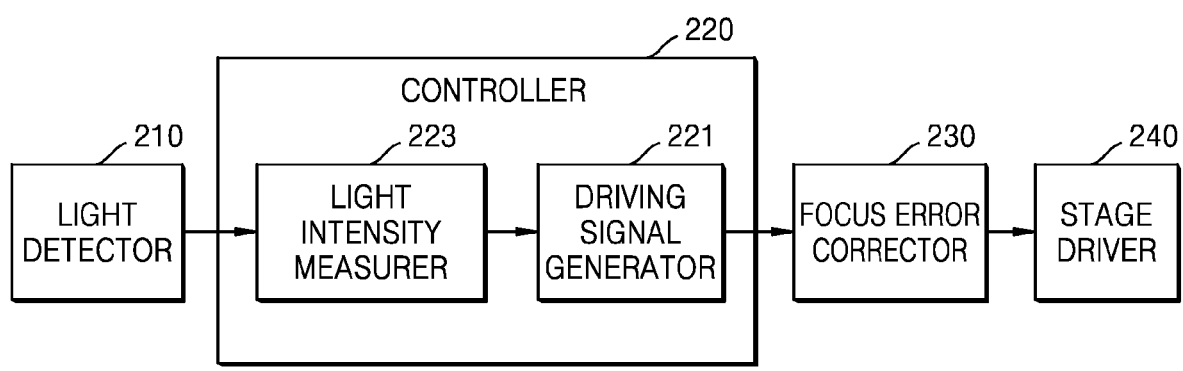
FIG. 3 is a block diagram showing an automatic focus controlling apparatus according to an example embodiment of inventive concepts.

FIG. 3 is a block diagram showing an automatic focus controlling apparatus according to an example embodiment of inventive concepts.

Referring to FIG. 1, the semiconductor inspection system 1 may include an observation optical system 100, an automatic focus controlling apparatus 200, and a wafer stage 170 supporting a wafer W. The observation optical system 100 may irradiate light onto an inspection surface of the wafer W and capture an image of the inspection surface by using an image capturer, such as a camera. Furthermore, the automatic focus controlling apparatus 200 adjusts a focal point of the light irradiated by the observation optical system 100 onto the inspection surface, thereby improving clarity of an image obtained via the image capturer.

The observation optical system 100 may include a light irradiator 110, an optical system 120, and an image capturer 130.

The light irradiator 110 may include an illumination light source that emits light toward the optical system 120. The optical system 120 may adjust an optical path of the light emitted by the light irradiator 110 by using a first beam splitter 121, a second beam splitter 123, and an object lens 125, such that the light emitted by the light irradiator 110 is irradiated onto a surface of the wafer W. The image capturer 130 may capture an image of the surface of the wafer W by using reflected light of the light irradiated onto and reflected by the surface of the wafer W. Furthermore, the reflected light may be incident to the automatic focus controlling apparatus 200 via the optical system 120.

Still referring to FIG. 1, the automatic focus controlling apparatus 200 may include a light detector 210, a controller 220, a focus error corrector 230, and a stage driver 240. The automatic focus controlling apparatus 200 may adjust a focal point of the observation optical system 100 by using the light reflected by the wafer W. The automatic focus controlling apparatus 200 may calculate a focus error of the observation optical system 100 and may feed a driving signal for correcting the focus error back to the stage driver 240.

The stage driver 240 moves the wafer stage 170 in directions including the x-axis direction, the y-axis direction, and the z-axis direction, and thus the wafer W may be moved in relation to the observation optical system 100 and the automatic focus controlling apparatus 200. The stage driver 240 may adjust the location of the wafer stage 170, such that the inspection surface of the wafer W may be suitably inspected via the observation optical system 100. The stage driver 240 may move the wafer stage 170 along an inspection path extending in the x-axis direction and the y-axis direction such that the images captured by the image capturer 130 are prevented and/or limited from overlapping. Furthermore, the stage driver 240 may adjust the z-axis directional location of the wafer stage 170 to set the focal point of the observation optical system 100 onto the inspection surface.

Here, a direction of a flat surface substantially parallel to the inspection surface of the wafer W is defined as the x-axis direction, a direction perpendicular to the x-axis direction on the flat surface is defined as the y-axis direction, and a direction perpendicular to both the x-axis direction and the y-axis direction is defined as the z-axis direction.

Referring to FIG. 2, the light detector 210 may receive the light reflected from an inspection surface of a wafer. The light detector 210 may output a voltage by using the incident light, and thus a light reception signal generated by the light detector 210 may have a voltage value.

According to an example embodiment, the light detector 210 may be a divided light receiving device having a light receiving surface that is divided into four light receiving components 212. For convenience of explanation, the four light receiving components 212 are sequentially indicated by the reference characters A, B, C, and D, where SA denotes a light reception signal generated by the light receiving component A. The four light receiving components 212 may have a same shape and a same size, where the light receiving component A and a light receiving component C may be arranged in a diagonal direction with respect to the light receiving surface such that the receiving components A and C may be opposite to each other, and a light receiving component B and a light receiving component D may be arranged in another diagonal direction with respect to the light receiving surface such that the receiving components B and D may be opposite to each other.

Referring to FIGS. 1 and 3, the controller 220 may include a light intensity measurer 223 and a driving signal generator 221.

The light intensity measurer 223 may measure brightness of the inspection surface of the wafer W by using a light reception signal generated by the light detector 210. The light intensity measurer 223 may generate a total intensity value SUM.

For example, a total light intensity value SUM generated by the light detector 210 consisting of the four light receiving components (212 of FIG. 2) is a sum of light reception signal values generated by the four light receiving components (212 of FIG. 2), where SUM=SA+SB+SC+SD (SA, SB, SC and SD being signal values for components A, B, C and D, respectively). A total light intensity value measured at highly reflective areas is larger than a total light intensity value measured at less reflective areas.

The driving signal generator 221 in the controller 220 may generate a driving signal for determining whether to perform automatic focus control. The driving signal may include an ON signal and an OFF signal. If an ON signal is generated, the z-axis directional location of a wafer stage may be adjusted. On the contrary, if an OFF signal is generated, the z-axis directional location of the wafer state may be held.

For example, if a total light intensity value measured by the light intensity measurer 223 is equal to or greater than a pre-set and/or selected reference value, the driving signal generator 221 may generate an ON signal. On the contrary, if a total light intensity value measured by the light intensity measurer 223 is smaller than the pre-set and/or selected reference value, the driving signal generator 221 may generate an OFF signal.

Here, a total light intensity value smaller than a pre-set and/or selected reference value may mean that reflectivity of the inspection surface of the wafer W is insufficient. If light used for automatic focus control is irradiated onto a surface of the wafer W with insufficient reflectivity, intensity of the light incident to the light detector 210 is significantly reduced and/or limited, and thus a focus error correcting signal may not be calculated.

In other words, the driving signal generator 221, as shown in FIG. 3, may determine whether an inspection point on the inspection surface of the wafer W is a highly reflective area or a less reflective area by using a total light intensity value transmitted from the light intensity measurer 223. The driving signal generator 221 generates an ON signal at a highly reflective area and performs automatic focus control. On the other hand, the driving signal generator 221 generates an OFF signal at a less reflective area and holds the z-axis directional location of the wafer stage 170 without performing automatic focus control. Here, according to at least some example embodiments, the reference value may be a predetermined and/or desired value that is between a light intensity value obtained at a highly reflective area of the inspection surface of the wafer W and a light intensity value obtained at a less reflective area of the inspection surface of the wafer W. That is, for example, the reference value may be an average value based on the light intensity value of the highly reflective area and the light intensity value of the less reflective area.

If the driving signal is an ON signal, the focus error corrector 230 may apply a focus error correcting signal for correcting a focus error of the observation optical system 100 to the stage driver 240. On the contrary, if the driving signal is an OFF signal, the focus error corrector 230 does not generate a focus error correcting signal. As a result, the z-axis directional location of the wafer stage 170 may be held.

According to example embodiments, when the driving signal is switched from an OFF signal to an ON signal, the z-axis directional location of the wafer stage 170 may be adjusted within about 2 micro-meters from the z-axis directional location of the wafer stage 170 corresponding to a time point before the OFF signal is switched to the ON signal.

Figure 4:
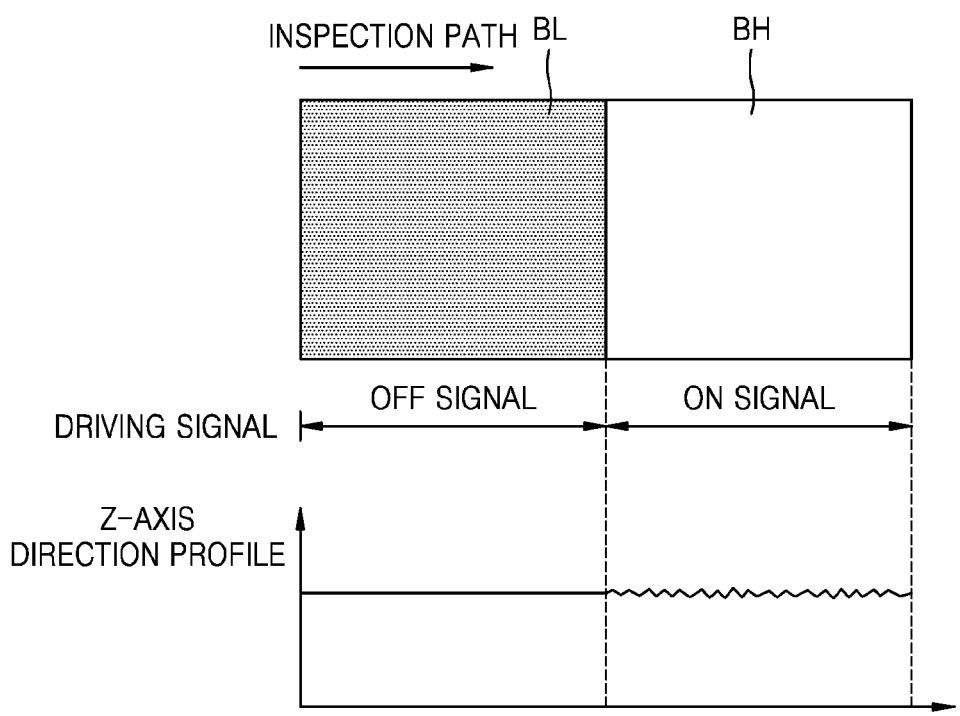
FIG. 4 is a diagram for describing automatic focus control performed on a portion of a wafer including a less reflective area and a highly reflective area.

FIG. 4 is a diagram for describing automatic focus control performed at a portion of a wafer including a less reflective area and a highly reflective area.

Referring to FIGS. 1, 3, and 4, and more particularly with respect to FIG. 4, the wafer W may include a less reflective area BL and a highly reflective area BH. FIG. 4 shows a case in which inspection is performed starting from the less reflective area and ending at the highly reflective area.

At the less reflective area BL, intensity of light reflected by the inspection surface of the wafer W decreases, and thus a total light intensity value measured by the light intensity measurer 223 becomes smaller than the reference value. Therefore, the driving signal generator 221 generates an OFF signal, and the focus error corrector 230 does not generate a focus error correcting signal in response to the OFF signal generated by the driving signal generator 221. As a result, the stage driver 240 does not adjust the z-axis directional location of the wafer stage 170, and as such, the wafer stage 170 may have a z-axis directional profile indicating a constant height level while an inspection is being performed at the less reflective area BL.

On the other hand, when an inspection point on the inspection surface of the wafer W moves out of the less reflective area BL and enters the highly reflective area BH, intensity of light reflected by the inspection surface increases. Therefore, a total light intensity value measured by the light intensity measurer 223 becomes greater than the reference value, and the driving signal generator 221 generates an ON signal. The focus error corrector 230 generates a focus error correcting signal in response to the ON signal generated by the driving signal generator 221, and as such, the stage driver 240 to which the focus error correcting signal is applied, may adjust the z-axis directional location of the wafer stage 170.

As a result, the z-axis directional profile of the wafer stage 170, while an inspection is being performed in the highly reflective area BH, may correspond to surface roughness of the inspection surface. The automatic focus controlling apparatus 200 may determine whether to perform automatic focus control based on the reflectivity of the inspection surface. Therefore, automatic focus control may be performed at the highly reflective area BH to obtain a clear image. Whereas, automatic focus control may not be performed at the less reflective area BL to prevent or limit a defocus.

Figure 5A:
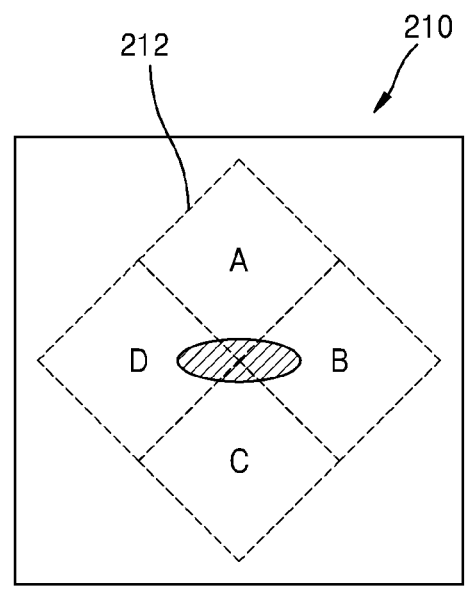
FIGS. 5A, 5B and 5C illustrate a diagram showing a light detector for describing a method of correcting a focus error according to an example embodiment of inventive concepts.
Figure 5B:
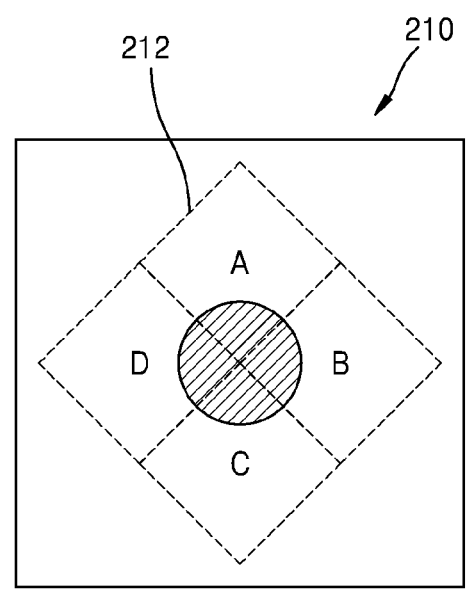
Figure 5C:
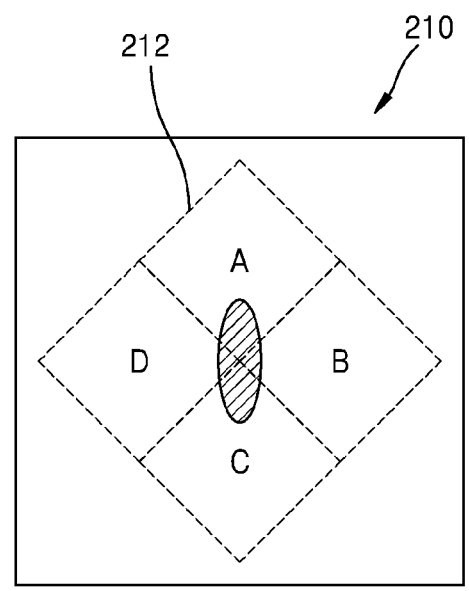

FIGS. 5A, 5B and 5C show a light detector for describing a method of correcting a focus error according to an example embodiment of inventive concepts.

Referring to FIGS. 1 and 5A to 5C the focus error corrector 230 may generate a focus error correcting signal by using astigmatism. Here, the focus error corrector 230 may utilize light reception signals from the light detector 210 including the light receiving surface consisting of the four light receiving components 212.

The astigmatism refers to a technique for detecting a distortion of an image formed by using an astigmatic optical system and measuring a displacement in the optical axis direction based on the same. For example, light incident to the light detector 210 may have a horizontally-long elliptical shape as shown in FIG. 5A, a circular shape as shown in FIG. 5B, or a vertically-long elliptical shape as shown in FIG. 5C.

The focus error corrector 230 may generate a focus error correcting signal value FE by using light reception signals generated by the four light receiving units 212, that is, SA, SB, SC, and SD, respectively, where the focus error correcting signal value may be defined as:

$$FE=(SA+SC)-(SB+SD)$$

In other words, the focus error correcting signal value may be a difference between a sum of light reception signals of light receiving components arranged in a diagonal direction from among the four light receiving components 212 and a sum of light reception signals of the other light receiving components arranged in another diagonal direction.

Referring to FIG. 5A, the reflected light having a horizontally-long elliptical shape is incident, where an amount of the reflected light incident to a light receiving component C is smaller than each amount of the reflected light incident to light receiving components B and D. Therefore, the light intensity value may have a negative value. In FIG. 5C, the reflected light having a vertically-long elliptical shape is incident, where amount of the reflected light incident to the light receiving component C is greater than each amount of the reflected light incident to the light receiving components B and D. Therefore, the light intensity value may have a positive value. Furthermore, in FIG. 5B, reflected light having a circular shape is incident, where amount of the reflected light incident to the light receiving component C may be almost identical to each amount of the reflected light incident to the light receiving components B and D. Therefore, the light intensity value may be close to 0.

In other words, the focus error corrector 230 may generate a focus error correcting signal value to set a light intensity value to 0 as shown in FIG. 5B. Based on the focus error correcting signal, the stage driver 240 may adjust the z-axis directional location of the wafer stage 170, such that the focal point of the observation optical system 100 is located on an inspection surface.

Figure 6:
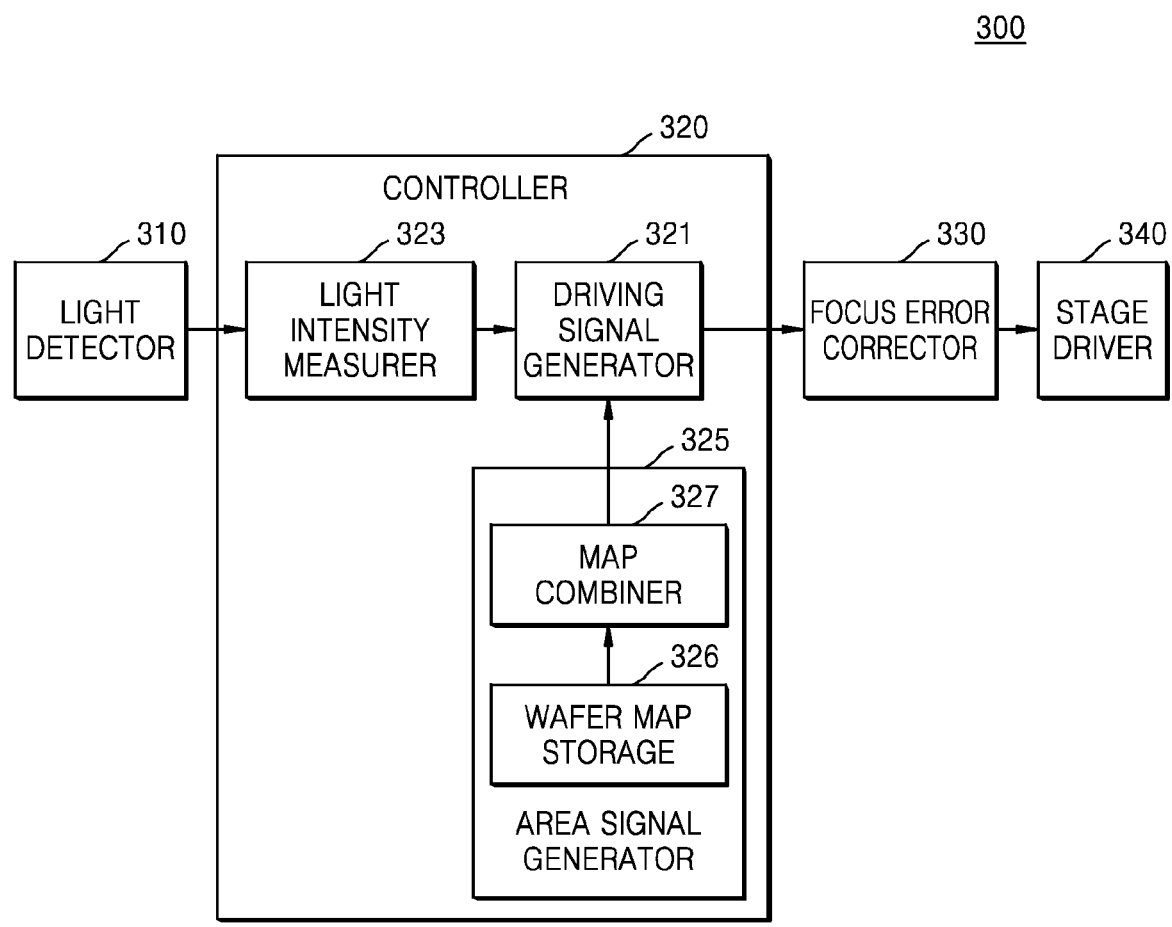
FIG. 6 is a block diagram showing an automatic focus controlling apparatus according to an example embodiment of inventive concepts.

FIG. 6 is a block diagram showing an automatic focus controlling apparatus 300 according to an example embodiment of inventive concepts.

Figure 7A:
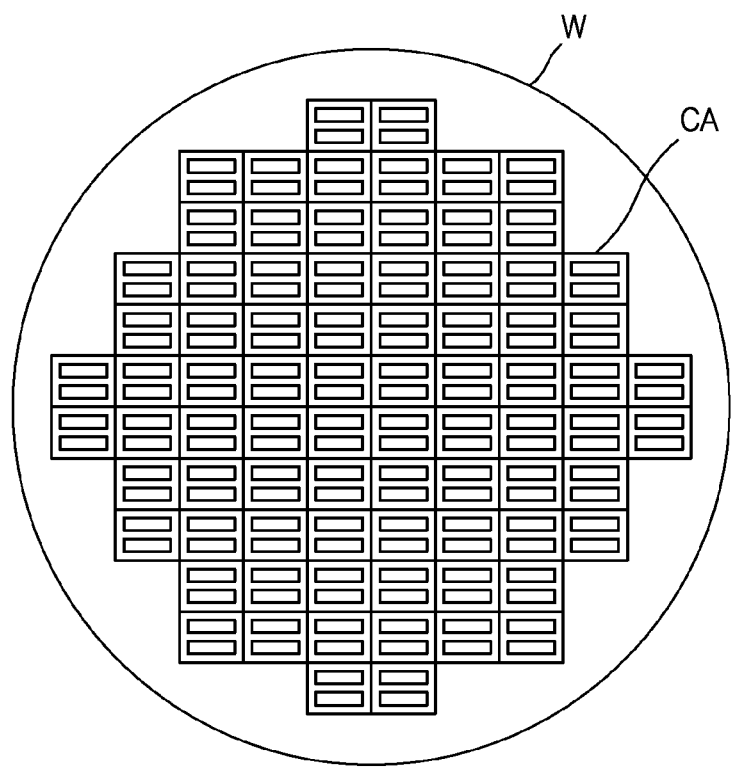
FIG. 7A is a schematic plan view of a surface of a wafer.
Figure 7B:
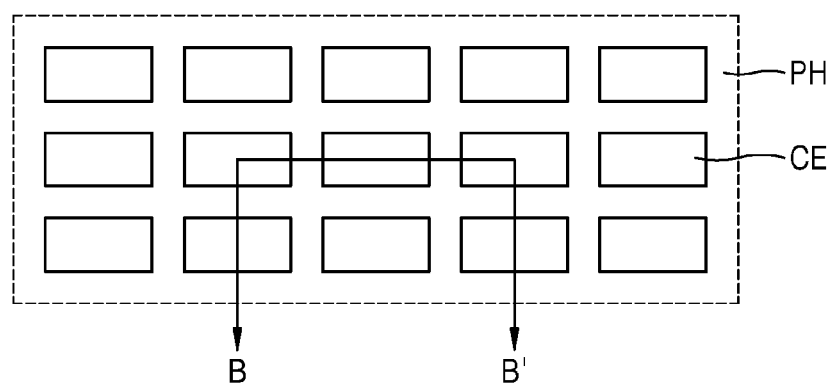
FIG. 7B is a schematic plan view of a portion of the surface of the wafer of FIG. 7A.
Figure 8:
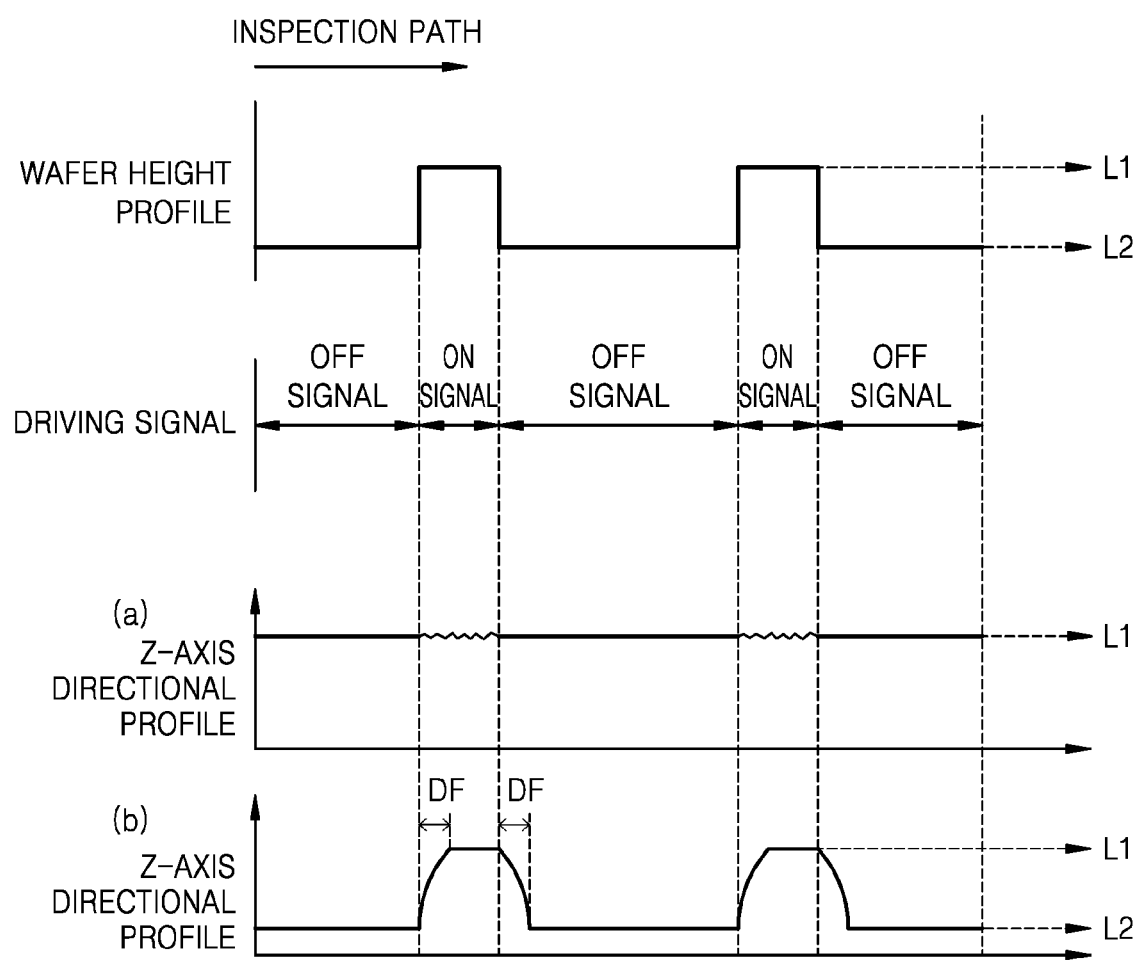
FIG. 8 is a diagram for describing automatic focus control performed at the area B-B' of FIG. 7B according to an example embodiment.

FIG. 7A is a schematic plan view of a surface of a wafer, and FIG. 7B is a schematic plan view of a portion of the surface of the wafer. FIG. 8 is a diagram for describing automatic focus control performed at the area B-B' of FIG. 7B.

Referring to FIG. 6, the automatic focus controlling apparatus 300 may include a light detector 310, a controller 320, a focus error corrector 330, and a stage driver 340. For convenience of explanation, descriptions identical to the descriptions given above with reference to FIGS. 1 to 5 will be given briefly or omitted.

Unlike the controller 220 shown in the example embodiment of FIG. 3, the controller 320 in the example embodiment of FIG. 6 may include an area signal generator 325 that applies an area signal to a driving signal generator 321. The area signal generator 325 may include wafer map storage 326 and a map combiner 327.

The area signal generator 325 may generate an area signal indicating whether an inspection point corresponding to a current time point is located at an inspection area or a non-inspection area. Here, an area signal corresponding to an inspection area indicates that the inspection point is located on the inspection area, whereas an area signal corresponding to a non-inspection area indicates that the inspection point is located on the non-inspection area.

If the area signal corresponds to the inspection area, the driving signal generator 321 generates an ON signal for adjusting the z-axis directional location of the stage driver 340. On the contrary, if the area signal corresponds to the non-inspection area, the driving signal generator 321 generates an OFF signal. In other words, if the inspection point is located at the inspection area, the automatic focus controlling apparatus 300 drives the stage driver 340 and adjusts the z-axis directional location of the wafer stage 170. On the contrary, if the inspection point moves out of the inspection area, the z-axis directional location of the wafer stage 170 may be held. Meanwhile, the driving signal generator 321 may be configured to generate a driving signal by using an area signal applied by the area signal generator 325 and a total light intensity value transmitted from the light intensity measurer 323.

In other words, the driving signal generator 321 may generate an ON signal when the total light intensity value is equal to or greater than a reference value and the area signal corresponds to the inspection area. Furthermore, the driving signal generator 321 may generate an OFF signal in a case where the total light intensity value is smaller than the reference value, and/or in a case where the area signal corresponds to the non-inspection area. However, unlike as shown in example embodiment of FIG. 6, the controller 320, according to an example embodiment, may generate the driving signal based on only one signal received from either the light intensity measurer 323 or the area signal generator 325. In other words, a driving signal may be generated by using a total light intensity value generated by the light intensity measurer 323 only, or may be generated by using an area signal generated by the area signal generator 325.

Referring to FIGS. 6 and 7A-B, and more particularly with respect to FIGS. 7A-B a wafer map indicates chip areas (CA) location coordinates of respective chips with respect to the inspection surface of the wafer W, and area location coordinates for identifying cell areas CE and peripheral areas PH in the chip areas CA may be stored in the wafer map storage 326 in advance. The chip areas (CA) location coordinates and the area location coordinates for identifying the cell areas CE and the peripheral areas PH may be coordinates determined in correspondence to an initial inspection location suggested before an inspection is performed.

The map combiner 327 shown in the example embodiment of FIG. 6 may generate an area signal corresponding to coordinates of an inspection point at which an inspection is being performed at a current time point by using the wafer map stored in the wafer map storage 326. Here, for example, the area signal may be a signal corresponding to an inspection area and/or a signal corresponding to a non-inspection area.

When the wafer stage (170 of FIG. 1) is moved in the x-axis direction or the y-axis direction, the map combiner 327 of FIG. 6 may calculate an x-axis directional displacement of the wafer stage 170, and a y-axis directional displacement of the wafer stage 170 by using moving speeds and moving times regarding the respective directions. The map combiner 327 may calculate coordinates of an inspection point corresponding to a current time point in relation to a suggested and/or desired initial inspection location.

Next, the map combiner 327 may determine whether coordinates of an inspection point corresponding to a current time point belong to an inspection area or a non-inspection area by using the chip areas (CA) location coordinates and the area location coordinates stored in the wafer map storage 326. Here, if an image capturing range of the image capturer (130 of FIG. 1) includes both the inspection area and the non-inspection area, the map combiner 327 may perform automatic focus control to focus at the inspection area by outputting an area signal corresponding to the inspection area.

Incidentally, in an inspection performed with respect to the wafer W, the initial inspection point may be located within the inspection area. The inspection area may be either the cell area CE or the peripheral area PH. For example, if the peripheral area PH corresponds to the inspection area and the cell area CE is set as the non-inspection area, the initial inspection point is located within the peripheral area PH. Here, the focal point of the observation optical system 100 is located at the initial inspection point on the inspection surface of the wafer W.

Referring to FIGS. 1, 6, 7A-B, and 8, and more particularly with respect to FIG. 8, the cell area CE and the peripheral area PH may have different height levels. For example, a height level L1 of the peripheral area PH may be greater than a height level L2 of the cell area CE. Here, automatic focus control performed when the peripheral area PH corresponds to the inspection area will be described. In an example embodiment, a height level of the inspection area is set to be greater than that of the non-inspection area.

While an inspection is being performed along an inspection path, a height profile of the inspection surface of the wafer W may be changed from a low level L2 to a high level L1 and may be changed from the high level L1 back to the low level L2. Here, a difference between the height level L1 of the peripheral area PH and the height level L2 of the cell area CE may have a value cell area exceeding an allowance range for preventing and/or limiting a defocus during automatic focus control.

First, the z-axis directional profile (b) of FIG. 8 indicates a z-axis directional profile of the wafer stage 170 in an example embodiment where automatic focus control is continuously performed at both the cell area CE and the peripheral area PH according to an example embodiment. In other words, in the z-axis directional profile (b), the driving signal generator 321 may generate ON signals when a height profile of the inspection surface of the wafer W changes from a low level L2 to a high level L1. Regarding the z-axis directional profile, a height change smaller than a difference between the height level L1 of the peripheral area PH and the height level L2 of the cell area CE is omitted for simplification.

The z-axis directional profile maintains the height level L2 of the cell area CE at the beginning of the inspection path and, as the inspection point enters the peripheral area PH, the z-axis directional profile raises to the height level L1 of the peripheral area PH. Here, it takes some time for the z-axis directional profile to rise in the initial entrance section DF to the peripheral area PH, where a defocus occurs during the time. In the same regard, when the height level decreases as the inspection point enters the cell area CE from the peripheral area PH, a defocus occurs during a time elapsed for the z-axis directional profile to decrease in the initial entrance section DF to the cell area CE.

In other words, a defocus occurs in the initial entrance section DF of the peripheral area PH when the inspection point enters the peripheral area PH from the cell area CE. On the contrary, if the cell area CE is the inspection area, a defocus occurs in the exit section of DF of the cell area CE when the inspection point enters the cell area CE from the peripheral area PH.

Meanwhile, the z-axis directional profile (a) of FIG. 8 indicates a z-axis directional profile of the wafer stage 170 in an example embodiment where an OFF signal is generated at the cell area CE (the non-inspection area) and automatic focus control is not performed at the cell area CE and an ON signal is generated at the peripheral area PH (the inspection area) and automatic focus control is performed at the peripheral area PH.

The driving signal generator 321 shown in FIG. 6 generates an OFF signal at the beginning of the inspection path, and thus the z-axis directional location of the wafer stage 170 may be held to maintain a constant height level. Here, the z-axis directional profile of the wafer stage 170 may be set to have the height level L1 of the peripheral area PH (the inspection area). Next, when the inspection point enters the peripheral area PH, automatic focus control is performed, and the z-axis directional location of the wafer stage 170 is adjusted in correspondence to surface roughness of the peripheral area PH. Next, when the inspection point enters the cell area CE from the peripheral area PH, automatic focus control is not performed, and thus the z-axis directional profile of the wafer stage 170 has the height level L1 of the peripheral area PH.

In other words, while an inspection is being performed with respect to a surface of the wafer W having different height levels, automatic focus control is not performed and the z-axis directional location of the wafer stage 170 is held at the non-inspection area, thereby preventing and/or limiting a defocus due to steps on the inspection surface of the wafer W.

According to example embodiments, when the driving signal is switched from an OFF signal to an ON signal, the z-axis directional location of the wafer stage 170 adjusted at the starting point of the ON signal as the ON signal is generated may be within about 2 micro-meters from the z-axis directional location of the wafer stage 170 corresponding to the OFF signal before the OFF signal is switched to the ON signal. In other words, by maintaining the height of the wafer stage 170 at the cell area CE, the height of the wafer stage 170 may be maintained to be almost equal to the height L1 of the peripheral area PH towards which the wafer stage 170 at the cell area CE continues in the z-axis direction.

Figure 9:
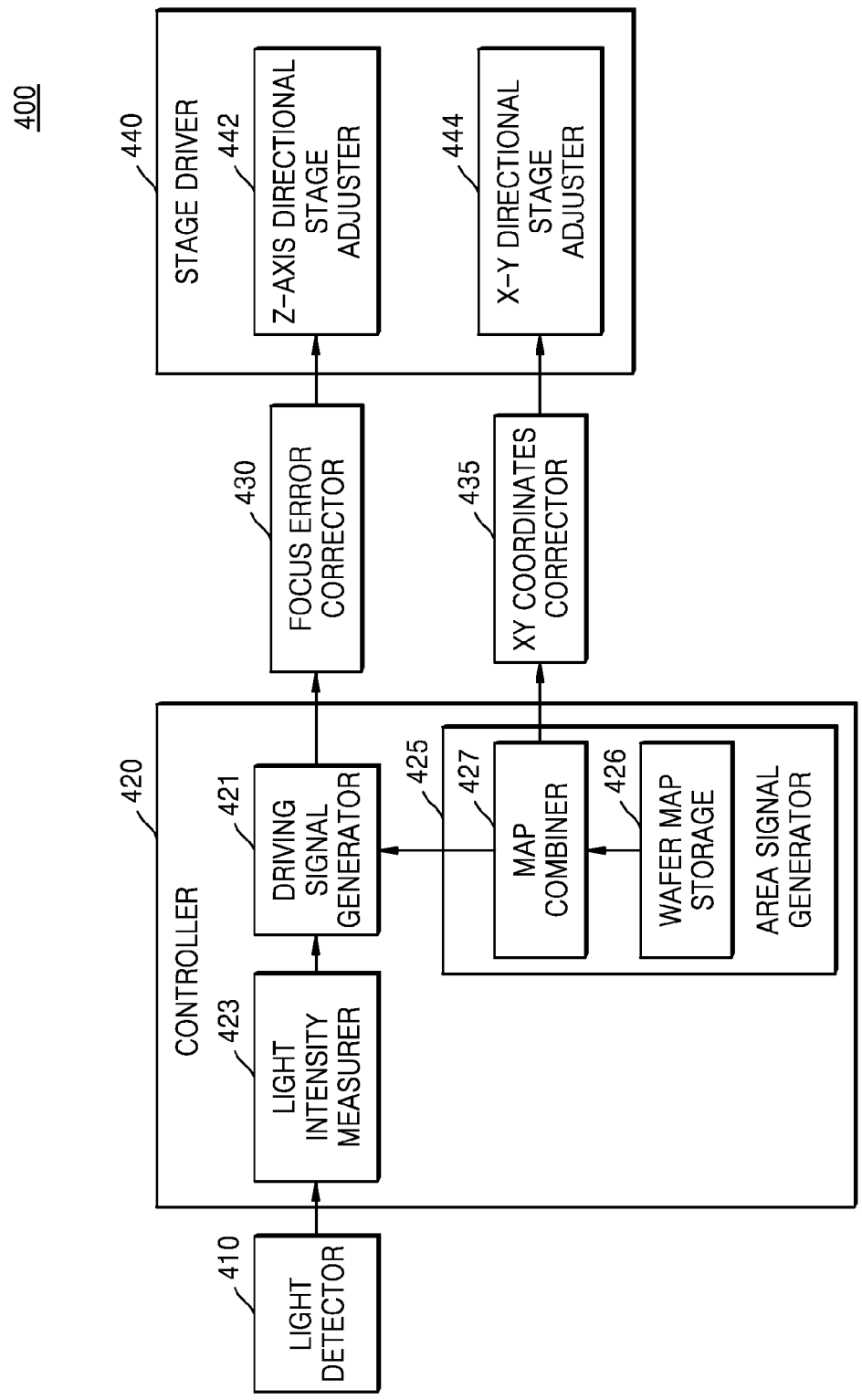
FIG. 9 is a block diagram showing an automatic focus controlling apparatus according to an example embodiment of inventive concepts.

FIG. 9 is a block diagram showing an automatic focus controlling apparatus 400 according to an example embodiment of inventive concepts.

Figure 10:
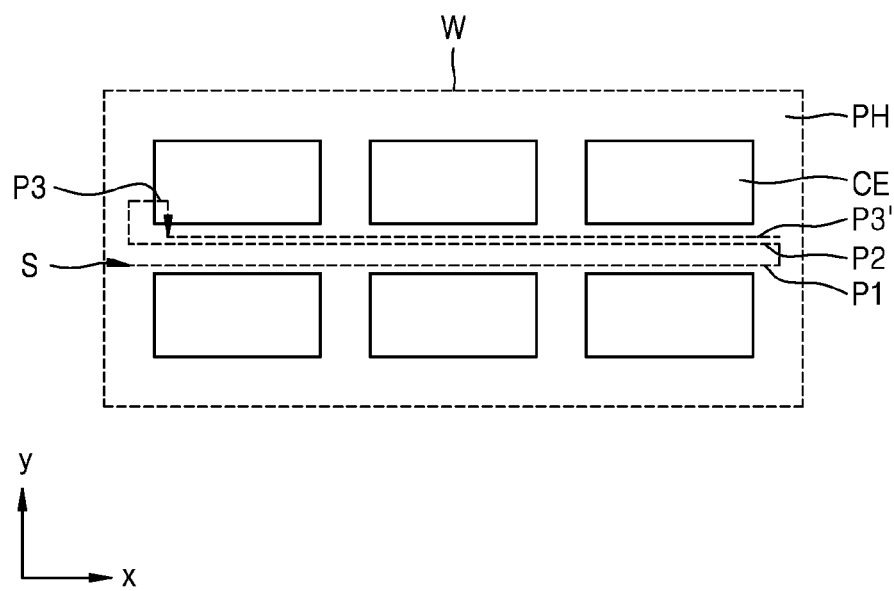
FIG. 10 is a schematic plan view of a portion of a surface of a wafer on which an inspection is being performed.

FIG. 10 is a schematic plan view of a portion of a surface of a wafer on which an inspection is being performed.

Referring to FIGS. 1 and 9, the automatic focus controlling apparatus 400 may include a light detector 410, a controller 420, a focus error corrector 430, an XY location corrector 435, and a stage driver 440. For convenience of explanation, descriptions identical to the descriptions given above will be given briefly or omitted.

The stage driver 440 may move the wafer stage 170 in directions including the x-axis direction, the y-axis direction, and the z-axis direction. The stage driver 440 may include a Z-axis directional stage adjuster 442 and an X-Y directional stage adjuster 444. The Z-axis directional stage adjuster 442 may receive a focus error correcting signal generated by the focus error corrector 430 and adjust the z-axis directional location of the wafer stage 170. Furthermore, the X-Y directional stage adjuster 444 may receive an X-Y location correcting signal generated by the XY location corrector 435 and adjust the x-axis directional location and the y-axis directional location of the wafer stage 170.

Unlike the controller 220 shown according to an example embodiment of FIG. 3, the controller 420 according to an example embodiment of FIG. 9 may include a driving signal generator 421 and an area signal generator 425 that applies an area signal with respect to the XY location corrector 435. The area signal generator 425 may include wafer map storage 326 and a map combiner 327.

The area signal generator 425 may generate an area signal indicating whether an inspection point corresponding to a current time point is located at an inspection area or a non-inspection area on an inspection surface of a wafer. Here, an area signal corresponding to an inspection area indicates that the inspection point is located on the inspection area, whereas an area signal corresponding to a non-inspection area indicates that the inspection point is located on the non-inspection area.

If the area signal corresponds to the inspection area, the driving signal generator 421 generates an ON signal for adjusting the z-axis directional location of the stage driver 440. On the contrary, if the area signal corresponds to the non-inspection area, the driving signal generator 421 generates an OFF signal. In other words, if the inspection point is at the inspection area, the automatic focus controlling apparatus 400 adjusts the z-axis directional location of the stage driver 440. On the contrary, if the inspection point is located out of the inspection area, the z-axis direction of the stage driver 440 is not adjusted.

Meanwhile, the driving signal generator 421 may be configured to generate a driving signal by using both an area signal applied by the area signal generator 425 and a total light intensity value transmitted by the light intensity measurer 423.

In other words, if the total light intensity value is greater than a reference value and the area signal corresponds to the inspection area, an ON signal may be generated. Furthermore, in any one of a case where the total light intensity value is smaller than the reference value and a case where the area signal corresponds to the non-inspection area, an OFF signal may be generated.

Meanwhile, the XY location corrector 435 may receive an area signal generated by the area signal generator 425 and generates an X-Y location correcting signal for correcting the x-axis directional location and the y-axis directional location of the stage driver 440. If the area signal corresponds to the non-inspection area, the XY location corrector 435 may apply an X-Y location correcting signal to the X-Y directional stage adjuster 444, such that the inspection point corresponding to a current time point is located on the inspection area.

However, the controller 420 of FIG. 9 may include only one from between the light intensity measurer 423 and the area signal generator 425. In other words, a driving signal may be generated by using a total light intensity value generated by the light intensity measurer 423 only or may be generated by using an area signal generated by the area signal generator 425.

If the controller 420 includes the area signal generator 425 only, adjustment of the z-axis directional location of the stage driver 440 is controlled based on an area signal. Furthermore, adjustments of the x-axis directional location and the y-axis directional location of the stage driver 440 may also be controlled based on the area signal.

Referring to FIG. 10, an inspection surface of a wafer W may include a cell area CE and a peripheral area PH, where an inspection regarding the inspection surface may be performed with respect to any one from between the cell area CE and the peripheral area PH. Here, a case in which an inspection regarding the inspection surface is performed with respect to the peripheral area PH will be described. In other words, the peripheral area PH corresponds to an inspection area, whereas the cell area CE corresponds to a non-inspection area.

For example, an inspection regarding the inspection surface of the wafer W may be performed by moving an inspection point along a first path P1 in the x-axis direction from an initial inspection point S, moving the inspection point for a certain distance in the y-axis direction, and moving the inspection point along a second path P2 that extends in a direction opposite to the first path P1. Here, the first path P1 and the second path P2 may be formed, such that areas captured by an image capturer (130 of FIG. 1) do not overlap.

A third path P3 continued from the second path P2 may enter the cell area CE (the non-inspection area). Here, the area signal generator 425 may apply an area signal indicating that the location of the inspection point corresponds to the non-inspection area to the XY location corrector 435.

The XY location corrector 435 may generate an X-Y location correcting signal for moving the coordinates of the inspection point to the peripheral area PH (the inspection area). Here, the X-Y location correcting signal may move the inspection point in the y-axis direction. As the location of the inspection point is changed in the y-axis direction based on the X-Y location correcting signal, the inspection regarding the inspection surface is performed along a modified path P3', where the modified path P3' is located on the peripheral area PH (the inspection area).

Although a range of the inspection performed along the modified path P3' may partially overlap a range of the inspection surface performed along the second path P2, a defocus due to a difference between height levels of the inspection area and the non-inspection area may be prevented and/or limited.

Figure 11:
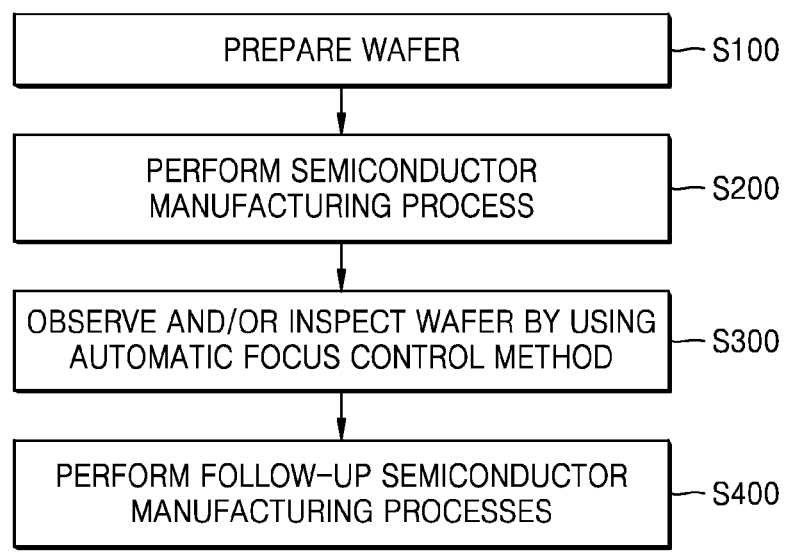
FIG. 11 is a flowchart showing a method of manufacturing a semiconductor device by using an automatic focus control method according to an example embodiment of inventive concepts.

FIG. 11 is a flowchart showing a method of manufacturing a semiconductor device by using an automatic focus control method according to an example embodiment of inventive concepts.

Referring to FIG. 11, at S100, a wafer for inspecting for a defect is prepared. Next, at S200, a semiconductor device manufacturing process is performed by using the wafer.

The semiconductor device manufacturing process may include formation of a thin-film. The thin-film may be formed of a conductive material, an insulation material, and/or a semiconductor material. The semiconductor device manufacturing process may further include formation of a mask pattern on the thin-film. The mask pattern may be a photoresist pattern. Furthermore, the semiconductor device manufacturing process may further include formation of a pattern by removing a portion of the thin-film by using the mask pattern as an etch mask. Alternatively, the semiconductor device manufacturing process may further include formation of a hole by removing a portion of the thin-film by using the mask pattern as an etch mask. The hole may include, for example, a contact hole, a via hole, and/or the like.

The semiconductor device manufacturing process may further include washing of the thin-film. Alternatively, the semiconductor device manufacturing process may further include planarization of the thin-film. The planarization of the thin-film may include a chemical mechanical polishing (CMP) process and/or an etch-back process. Furthermore, although not stated above, the semiconductor device manufacturing process may include all processes that may be performed during manufacturing of a semiconductor device. Therefore, the semiconductor device manufacturing process may also include transferring of a semiconductor substrate and storage of the semiconductor substrate.

The semiconductor device manufacturing process may include inspection and/or observation of a surface of the wafer. At S300, the inspection and/or observation of the wafer may be performed after any one of the above-stated processes of the semiconductor device manufacturing process is performed. The inspection and/or observation may be performed by using the automatic focus controlling apparatus described above with reference to FIGS. 1 to 10.

If it is determined in the inspection that there is no defect on the wafer, at S400, follow-up processes of the semiconductor device manufacturing process may be performed.

In other words, in the semiconductor device manufacturing process according to an example embodiment of inventive concepts, defects on a surface of a wafer may be inspected by using the automatic focus control apparatus and the automatic focus control method as described above.

Figure 12:
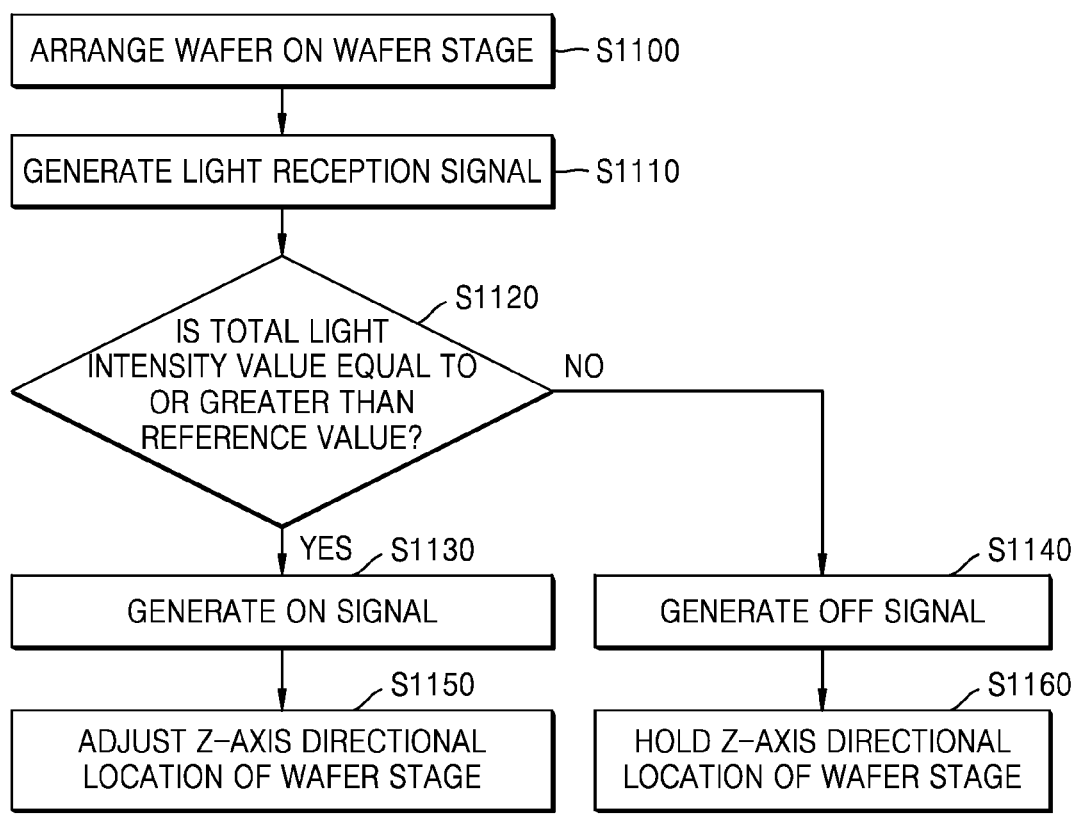
FIG. 12 is a flowchart for describing a method of inspecting a wafer according to an example embodiment by using the automatic focus control method of FIG. 11.

FIG. 12 is a flowchart for describing a method of inspecting a wafer by using the automatic focus control method of FIG. 11.

Referring to FIGS. 1 to 3 and 12, and more particularly with respect to FIG. 12, the automatic focus control method may include the procedure as described below. First, at S1100, a wafer W to be inspected is arranged on a wafer stage 170.

Next, at S1110, light is irradiated onto an inspection surface of the wafer W and a light reception signal is generated by receiving reflected light reflected by the inspection surface.

An observation optical system 100 irradiates light onto an inspection point on the inspection surface of the wafer W, and reflected light reflected by the inspection surface is incident to a light detector 210 via the observation optical system 100. The light detector 210 may consist of a split light receiving device split into four light receiving components 212, where the light detector 210 may generate a light reception signal having a voltage value corresponding to intensity of the incident reflected light.

Next, at S1120, a total light intensity value of the reflected light incident to the light detector 210 is compared to a reference value, and a driving signal is generated.

The total light intensity value SUM may be calculated by summing light reception signals generated by the four light receiving units 212, respectively. If the total light intensity value is equal to or greater than a pre-set and/or selected reference value, the driving signal generator 221, at S1130, generates an ON signal. At S1150, a focus error corrector 230 generates a focus error correcting signal in response to the ON signal, and the stage driver 240, to which the focus error correcting signal is applied, performs automatic focus control for adjusting the z-axis directional location of the wafer stage 170.

On the contrary, if the total light intensity value is smaller than or equal to a pre-set and/or selected reference value, the driving signal generator 221, at S1140, generates an OFF signal. The focus error corrector 230 does not generate a focus error correcting signal in response to the OFF signal, and the stage driver 240, at S1160, holds the z-axis directional location of the wafer stage 170.

Here, the reference value may be set before the inspection is performed with respect to the inspection surface of the wafer W. For example, a light intensity value of a highly reflective area on the inspection surface at which automatic focus control may be performed and a light intensity value of a less reflective area at which a defocus occurs may be measured, and an average value based on the light intensity value regarding the highly reflective area and the light intensity value of the less reflective area may be determined as the reference value.

Figure 13:
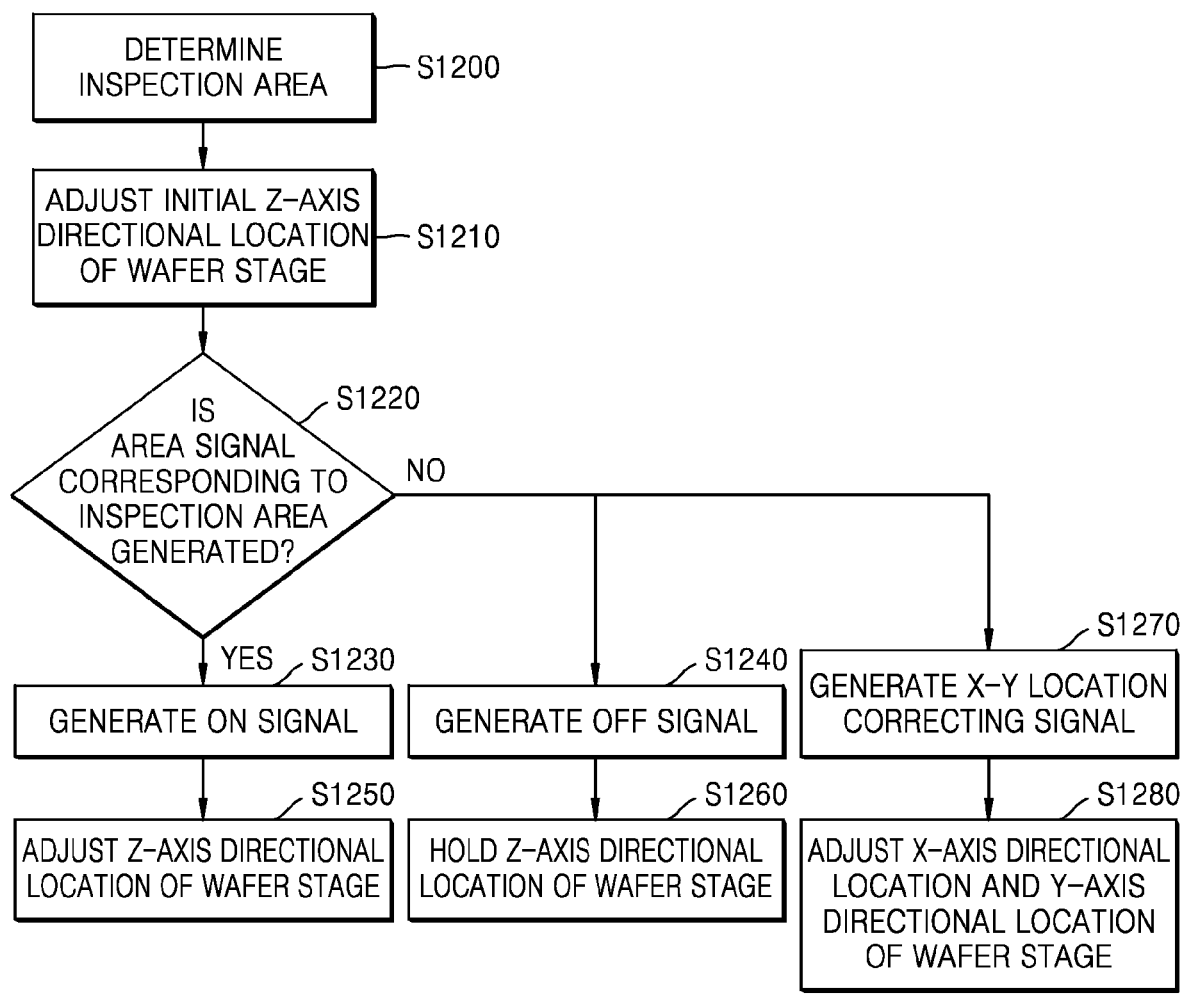
FIG. 13 is a flowchart for describing a method of inspecting a wafer according to an example embodiment by using the automatic focus control method of FIG. 11.

FIG. 13 is a flowchart for describing a method of inspecting a wafer by using the automatic focus control method of FIG. 11.

Referring to FIGS. 6 to 8 and 13, and more particularly with respect to FIG. 13, the automatic focus control method may include the procedure as described below. First, at S1200, an inspection area and a non-inspection area are determined by using a wafer map.

The wafer map may include information regarding chip areas (CA) location coordinates regarding an inspection surface of the wafer W and area location coordinates for identifying cell areas CE and peripheral areas PH in the cell areas CA. Before an inspection is performed with respect to the inspection surface of the wafer W, the inspection area for performing the inspection may be determined.

At S1210, the initial z-axis directional location of a wafer stage (170 of FIG. 1) is adjusted, such that focus is set to the wafer stage 170 at an initial inspection point. The inspection point may be suggested within the inspection area, and an automatic focus controlling apparatus 300 adjusts the initial z-axis directional location of the wafer stage 170 to remove a focus error of an observation optical system (100 of FIG. 1).

Next, at S1220, coordinates of the inspection point corresponding to a current time point are obtained, an area signal is generated, and it is determined whether the area signal corresponds to the inspection area or the non-inspection area.

The inspection regarding the inspection surface is performed by moving the inspection point from the initial inspection point in the x-axis direction or the y-axis direction. Here, in relation to the initial inspection point, an x-axis directional displacement and a y-axis directional displacement regarding coordinates of the inspection point corresponding to a current time point may be calculated by using moving speeds and moving times in respective directions. If the inspection point corresponding to the current time point belongs to the inspection area, an area signal corresponding to the inspection area is generated. On the contrary, if the inspection point corresponding to the current time point belongs to the non-inspection area, an area signal corresponding to the non-inspection area is generated.

If the inspection point is located within the inspection area, the area signal generator 325, at S1230, generates an area signal corresponding to the inspection area. When the area signal corresponding to the inspection area is applied to the driving signal generator 321, the driving signal generator 321 generates an ON signal. Therefore, the stage driver 340, at S1250, performs automatic focus control for adjusting the z-axis directional location of the wafer stage (170 of FIG. 1).

On the contrary, the inspection point is located within the non-inspection area, the area signal generator 325, at S1240, generates an area signal corresponding to the non-inspection area. When the area signal corresponding to the non-inspection area is applied to the driving signal generator 321, the driving signal generator 321 generates an OFF signal. Therefore, the stage driver 340, at S1260, holds the z-axis directional location of the wafer stage 170.

In other words, when the inspection is initiated, the automatic focus controlling apparatus 300 adjusts the z-axis directional location of the wafer stage 170, such that the initial inspection point is focused by the observation optical system (100 of FIG. 1). Next, while the inspection is being performed in the inspection area, automatic focus control is performed, and thus a clear inspection image may be obtained. Furthermore, when the inspection point enters the non-inspection area, the wafer stage 170 holds the z-axis directional location of the wafer stage 170, such that the z-axis directional location of the wafer stage 170 is close to a height level of the inspection area. Therefore, a defocus in an initial entrance section via which the inspection point enters the inspection area from the non-inspection area is prevented and/or limited.

Meanwhile, referring to FIGS. 9 and 13, if an area signal corresponding to the non-inspection area is generated by an area signal generator 425, the XY location corrector 435, at S1270, may generate an X-Y location correcting signal. The X-Y location correcting signal is applied to a stage driver 440, and the stage driver 440, at S1280, may adjust the x-axis directional location and the y-axis directional location of the wafer stage (170 of FIG. 1), such that the inspection point is located within the inspection area.

The controller 220, focus error corrector 230, drive signal generator 221, controller 320, driving signal generator 321, area signal generator 325, map combiner 327, wafer map storage 326, focus error corrector 330, controller 420, driving signal generator 421, area signal generator 425, map combiner 427, wafer map storage 426, and focus error corrector 430 may be hardware, firmware, hardware executing software or any combination thereof. When at least one of the aforementioned components is hardware, such existing hardware may include one or more Central Processing Units (CPUs), digital signal processors (DSPs), application-specific-integrated-circuits (ASICs), field programmable gate arrays (FPGAs) computers or the like configured as special purpose machines to perform the functions of the at least one of the aforementioned components. CPUs, DSPs, ASICs and FPGAs may generally be referred to as processors and/or microprocessors.

In the event where at least one of the aforementioned components is a processor executing software, the processor is configured as a special purpose machine to execute the software to perform the functions of the at least one of the aforementioned components. In such an embodiment, the processor may include one or more Central Processing Units (CPUs), digital signal processors (DSPs), application-specific-integrated-circuits (ASICs), and/or field programmable gate arrays (FPGAs) computers.

While inventive concepts have been particularly shown and described with reference to example embodiments thereof, it will be understood that various changes in form and details may be made therein without departing from the spirit and scope of the following claims.

What is claimed is:

1. A focus control apparatus comprising:
   a light detector configured to,
      receive light reflected by a surface of a wafer, and
      generate a light reception signal based on the received light;
   a controller configured to,
      generate a driving signal based on whether an intensity value of the received light is equal to or greater than a reference value, the driving signal being one of a first signal and a second signal, the driving signal indicating whether to perform focus control based on the light reception signal;
   a focus error corrector configured to,
      generate a focus error correction signal based on the driving signal; and
   a stage driver configured to,
      displace a wafer stage supporting the wafer by adjusting a z-axis position of the wafer stage based on the focus error correction signal if the driving signal is the first signal, and
      maintain the z-axis position of the wafer stage based on the focus error correction signal if the driving signal is the second signal.

2. The focus control apparatus of claim 1, wherein the focus error corrector is further configured to,
   generate the focus error correction signal if the driving signal is the first signal, and
   not generate the focus error correction signal if the driving signal is the second signal.

3. The focus control apparatus of claim 1, wherein the stage driver is further configured to,
   adjust the z-axis position of the wafer stage if the driving signal is switched from the second signal to the first signal such that the z-axis position is adjusted within 2 micro-meters from the z-axis position of the wafer stage corresponding to a time point before the second signal is switched to the first signal.

4. The focus control apparatus of claim 1, wherein the controller comprises:
   a light intensity measurer configured to measure a light intensity of light incident to the light detector; and
   a driving signal generator configured to,
      generate the first signal if the light intensity is equal to or greater than the reference value, and
      generate the second signal if the light intensity is smaller than the reference value.

5. The focus control apparatus of claim 4, wherein the light detector includes,
   light receiving components, and
   a light receiving surface divided among the light receiving components; and the light intensity measurer is further configured to calculate a light intensity value by summing light intensities measured by the light receiving components.

6. The focus control apparatus of claim 1, wherein the controller comprises:
an area signal generator configured to generate an area signal based on a location of an inspection point on an inspection surface, the area signal corresponding to an inspection area or a non-inspection area of the wafer; and
a driving signal generator configured to,
generate the first signal if the area signal corresponds to the inspection area, and
generate the second signal if the area signal corresponds to the non-inspection area.

7. The focus control apparatus of claim 6, wherein the area signal generator comprises:
a wafer map storage device storing location coordinates of the inspection area and the non-inspection area; and
a map combiner configured to generate the area signal corresponding to the location of the inspection point based on the location coordinates.

8. The focus control apparatus of claim 6, further comprising:
an XY location corrector configured to,
receive the area signal, and
generate an X-Y location correction signal if the area signal corresponds to the non-inspection area,
wherein the stage driver is further configured to adjust one of an x-axis position or a y-axis position of the wafer stage based on the X-Y location correction signal.

9. The focus control apparatus of claim 1, wherein the controller comprises:
a light intensity measurer configured to measure the intensity value;
an area signal generator configured to generate an area signal based on a location of an inspection point on the surface of the wafer, the area signal corresponding to an inspection area or a non-inspection area; and
a driving signal generator configured to,
generate the first signal if the intensity value is equal to or greater than a reference value and the area signal corresponds to the inspection area, and
generate the second signal if the intensity value is smaller than the reference value or the area signal corresponds to the non-inspection area.

10. A focus controlling apparatus, comprising:
a controller configured to,
measure an intensity value of light reflected from a surface of a wafer, and
determine whether to perform focus control on the wafer based on at least one of (i) the measured intensity value of the light reflected being equal to or greater than a reference value and (ii) an inspection point on the wafer being within an inspection area; and
a stage driver configured to adjust a z-axis position of a wafer stage based on the determination, the wafer on the wafer stage.

11. The focus controlling apparatus of claim 10, wherein the controller is further configured to output a driving signal based on the determination, the driving signal being one of a first signal and a second signal.

12. The focus controlling apparatus of claim 11, wherein the first signal is generated by the controller if (i) the measured intensity value of the light reflected is equal to or greater than the reference value, and (ii) the inspection point on the wafer is in the inspection area, and
the second signal is outputted by the controller if (i) the measured intensity value of the light reflected is less than the reference value, or (ii) the inspection point on the wafer is in a non-inspection area.

13. The focus controlling apparatus of claim 12, wherein the controller includes an area signal generator, the area signal generator configured to generate an area signal, the area signal corresponds to coordinates of the inspection point at which an inspection is performed based on a wafer map, and the area signal indicates whether the inspection point on the wafer is within the inspection area.

14. The focus controlling apparatus of claim 11, further comprises:
a focus error corrector configured to generate a focus error correcting signal based on the driving signal; and
a location correction configured to generate a location correcting signal based on an area signal corresponding to a non-inspection area,
wherein the stage driver is further configured to,
adjust the z-axis position of the wafer stage based on the focus error correcting signal, and
adjust x and y axis positions of the wafer stage based on the location correcting signal.

* * * * *